United States Patent
Cho et al.

(10) Patent No.: US 9,874,474 B2
(45) Date of Patent: Jan. 23, 2018

(54) BIOMETRIC SENSOR AND BIOMETRIC ANALYSIS SYSTEM INCLUDING THE SAME

(71) Applicants: SAMSUNG ELECTRONICS CO., LTD., Suwon-si (KR); IMEC TAIWAN, Hsinchu (TW)

(72) Inventors: Seongho Cho, Gwacheon-si (KR); Chaokang Liao, Hsinchu (TW); Dongho Kim, Seoul (KR)

(73) Assignees: SAMSUNG ELECTRONICS CO., LTD., Suwon-si (KR); IMEC TAIWAN, Hsinchu (TW)

( * ) Notice: Subject to any disclaimer, the term of this patent is extended or adjusted under 35 U.S.C. 154(b) by 0 days.

(21) Appl. No.: 15/058,693

(22) Filed: Mar. 2, 2016

(65) Prior Publication Data

US 2016/0258814 A1    Sep. 8, 2016

(30) Foreign Application Priority Data

Mar. 2, 2015  (KR) .................. 10-2015-0029203

(51) Int. Cl.
| | |
|---|---|
| *G01J 3/00* | (2006.01) |
| *G01J 3/42* | (2006.01) |
| *G01J 3/02* | (2006.01) |
| *G01J 3/10* | (2006.01) |
| *A61B 5/00* | (2006.01) |
| *A61B 5/145* | (2006.01) |
| *A61B 5/1455* | (2006.01) |

(52) U.S. Cl.
CPC .............. *G01J 3/42* (2013.01); *A61B 5/0075* (2013.01); *G01J 3/0208* (2013.01); *G01J 3/0243* (2013.01); *G01J 3/0291* (2013.01); *G01J 3/108* (2013.01); *A61B 5/1455* (2013.01); *A61B 5/14532* (2013.01); *A61B 2560/045* (2013.01)

(58) Field of Classification Search
CPC ...... G01J 3/02; G01J 3/28; G01J 3/42; G01N 21/31; G01N 21/552
USPC ......................................................... 356/300
See application file for complete search history.

(56) References Cited

U.S. PATENT DOCUMENTS

| | | | |
|---|---|---|---|
| 6,828,809 B1 | 12/2004 | Bruce et al. | |
| 2003/0023152 A1* | 1/2003 | Abbink ............... | A61B 5/0075 600/316 |
| 2008/0147053 A1 | 6/2008 | Kang et al. | |
| 2009/0002718 A1 | 1/2009 | Wadman | |

(Continued)

FOREIGN PATENT DOCUMENTS

| | | |
|---|---|---|
| JP | 2006526428 A | 11/2006 |
| KR | 1020080056034 A | 6/2008 |
| KR | 1020080090452 A | 10/2008 |

*Primary Examiner* — Tarifur Chowdhury
*Assistant Examiner* — Md M Rahman
(74) *Attorney, Agent, or Firm* — Sughrue Mion, PLLC

(57) ABSTRACT

A biometric sensor that measures biometric information and a biometric analysis system including the biometric sensor are provided. The biometric sensor may include: a light source configured to emit light toward a region of interest of an object under examination, the light being diffused at the region of interest; a collimator that includes a though-hole and is configured to collimate the diffused light received from the region of interest; and a spectrometer configure to analyze the diffused light transmitted by the collimator.

5 Claims, 4 Drawing Sheets

(56) References Cited

U.S. PATENT DOCUMENTS

| | | | |
|---|---|---|---|
| 2012/0035442 A1* | 2/2012 | Barman | A61B 5/14532 600/316 |
| 2012/0118974 A1* | 5/2012 | Germaine | G06K 7/1452 235/462.27 |
| 2012/0133932 A1 | 5/2012 | Henry et al. | |
| 2013/0188181 A1* | 7/2013 | Angel | G01J 3/44 356/301 |
| 2013/0210058 A1* | 8/2013 | White | A61B 5/0082 435/29 |

* cited by examiner

BIOMETRIC SENSOR AND BIOMETRIC ANALYSIS SYSTEM INCLUDING THE SAME

CROSS-REFERENCE TO RELATED APPLICATION

This application claims priority from Korean Patent Application No. 10-2015-0029203, filed on Mar. 2, 2015 in the Korean Intellectual Property Office, the disclosure of which is incorporated herein by reference in its entirety.

BACKGROUND

1. Field

Apparatuses and methods consistent with exemplary relate to biometric sensors and biometric analysis systems including the same, and more particularly, to biometric sensors detecting light that is reflected from an object under examination after being incident thereto and biometric analysis systems for analyzing information obtained from the biometric sensors.

2. Description of the Related Art

Due to technical developments, near-infrared spectrometers and Raman spectrometers have become smaller. In the related art, measurement of biometric information may be restricted to certain regions of a human body under examination. However, small-sized near-infrared spectrometers and Raman spectrometers may allow biometric information to be measured from various body parts.

In order to obtain biometric information from an object under examination, light may be emitted onto the object so that the emitted light is reflected from the object, and biometric information is obtained from the reflected light. The light that includes biometric information may be diffused in all directions, and in a process of inputting the light that includes biometric information, light loss may be accompanied. Thus, in order to obtain a high efficiency spectrum and to increase a signal-to-noise ratio, there may be a need for minimizing loss of diffused light. For example, when Raman spectroscopy is used, since frequency of photons includes biometric information, it may be important to reduce loss of light caused by diffusion.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide biometric sensors that transmit diffused light that includes biometric information to a spectrometer with reduced light loss.

Further, one or more exemplary embodiments provide biometric analysis systems that include the biometric sensors.

According to an aspect of an exemplary embodiment, there is provided a biometric sensor including: a light source configured to emit light toward a region of interest of an object under examination, the light being diffused at the region of interest; a collimator that comprises a though-hole and is configured to collimate the diffused light received via the through-hole; and a spectrometer configured to analyze the diffused light transmitted by the collimator.

The biometric sensor may further include a focus lens configured to control a focal distance of the emitted light.

The emitted light may have a wavelength in a range from about 0.7 µm to about 2.5 µm.

The emitted light may be focused on the through-hole of the collimator by the focus lens.

The biometric sensor may further include an optical path converter configured to control an optical path of the emitted light.

The collimator may include an opening via which the emitted light is incident on the region of interest.

The collimator may be a compound parabolic concentrator (CPC) type collimator.

According to an aspect of another exemplary embodiment, there is provided a biometric analysis system including: a light source configured to emit light toward a region of interest of an object under examination, the light being diffused at the region of interest; a collimator that includes a through-hole and is configured to collimate the diffused light received via the through-hole; a spectrometer configured to analyze the diffused light transmitted by the collimator; and a controller configured to analyze biometric information of the object obtained from the analyzed diffused light.

The controller may include: a signal processor configured to analyze the biometric information of the object based on a signal provided to the controller by the spectrometer; and a user interface configured to communicate with the signal processor.

The user interface may include: an input unit configured to input a command during an analysis of the biometric information and a display configured to display a result of the analysis of the biometric information.

The biometric analysis system may further include a storage configured to store the analyzed biometric information.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
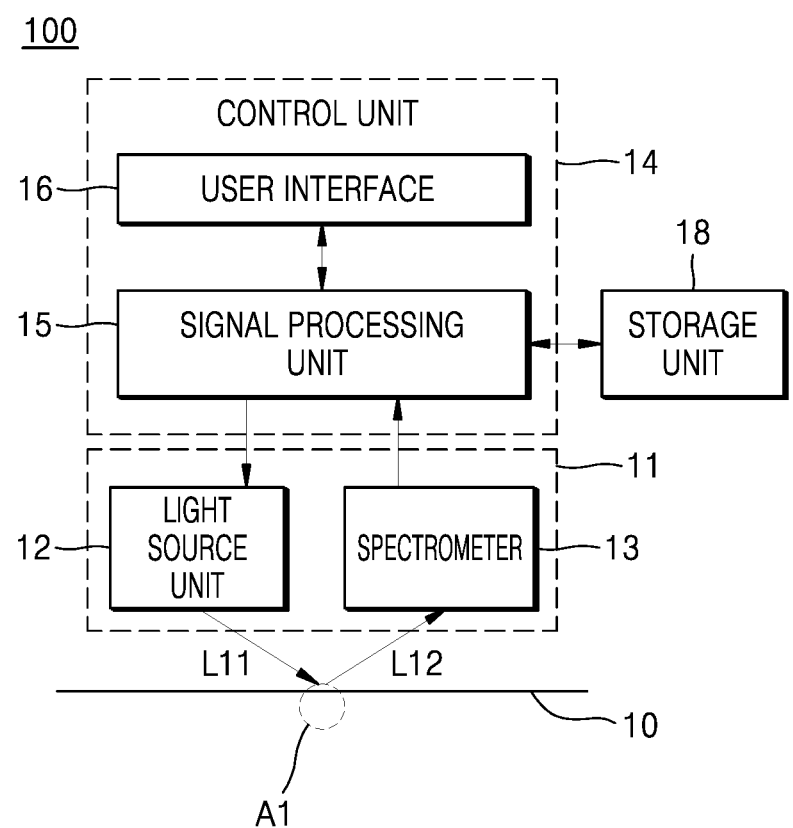
FIG. 1 illustrates a biometric analysis system according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

In describing layer structures, when an element or layer is referred to as being "on" another element or layer, the element or layer may be directly on another element or layer or intervening elements or layers.

FIG. 1 illustrates a biometric analysis system 100 according to an exemplary embodiment.

Referring to FIG. 1, the biometric analysis system 100 may include a biometric sensor 11 and a control unit (e.g., controller) 14. The biometric sensor 11 may emit light L11 onto a region A1 of interest of an object 10 under examination and acquire diffused light L12 that is reflected from the region A1 of interest. The control unit 14 may analyze biometric information of the object 10 by using the diffused light L12 obtained from the biometric sensor 11. The biometric sensor 11 may include a light source unit (e.g., light source) 12 that emits the light L11 to the object 10 and a spectrometer 13 that measures the diffused light L12 generated from the region A1 of interest. The control unit 14 may include a signal processing unit (e.g., signal processor) 15 and a user interface 16. Also, the biometric analysis system 100 may further include a storage unit (e.g., storage or memory) 18 that stores the biometric information of the object 10 that is processed in the signal processing unit 15.

The biometric sensor 11 used in the biometric analysis system 100 according to an exemplary embodiment is a non-invasive biometric sensor and may include the light source unit 12 and the spectrometer 13, which will be described in detail below. The light L11 may be emitted from the light source unit 12 of the biometric sensor 11 onto the region A1 of interest of the object 10. The type of the light L11 may be selected in connection with biometric information to be obtained from the object 10 under examination. For example, the light source unit 12 may emit light of near infrared region having a wavelength in a range from about 0.7 μm to about 2.5 μm. A light source used in the light source unit 12 may include a light emitted diode (LED) or a laser diode.

The light L11 may collide with a surface and internal molecular structure of the object 10 under examination, and may become a diffused light L12, a wavelength of which is changed when the diffused light L12 is re-emitted after being absorbed in the molecular structure. The diffused light L12 may include various spectrums due to different degrees of wavelength transformation according to the state of molecules that constitute the region A1 of interest of the object 10. Accordingly, the diffused light L12 emitted from the region A1 of interest may include biometric information of the region A1 of interest, and thus, biometric information (e.g., blood glucose contents) may be obtained by analyzing the diffused light L12.

The light L12 may be diffused in all directions, and thus, in order to correctly detect the biometric information of the object 10, the diffused light L12 may be required to be transmitted to the spectrometer 13 with minimum loss. Accordingly, a collimator may be included in the biometric sensor 11 to collimate the direction of the diffused light L12 reflected from the object 10 in a constant direction towards the spectrometer 13. An optical reflection material layer to reflect the diffused light L12 towards the spectrometer 13 may be formed in the collimator, and the optical reflection material layer may have a compound parabolic concentrator (CPC) shape. The biometric sensor 11 according to an exemplary embodiment employs an optical system structure by which the light L11 is emitted onto the region A1 of interest and the diffused light L12 reflected from the region A1 of interest may be input to the spectrometer 13.

Figure 2:
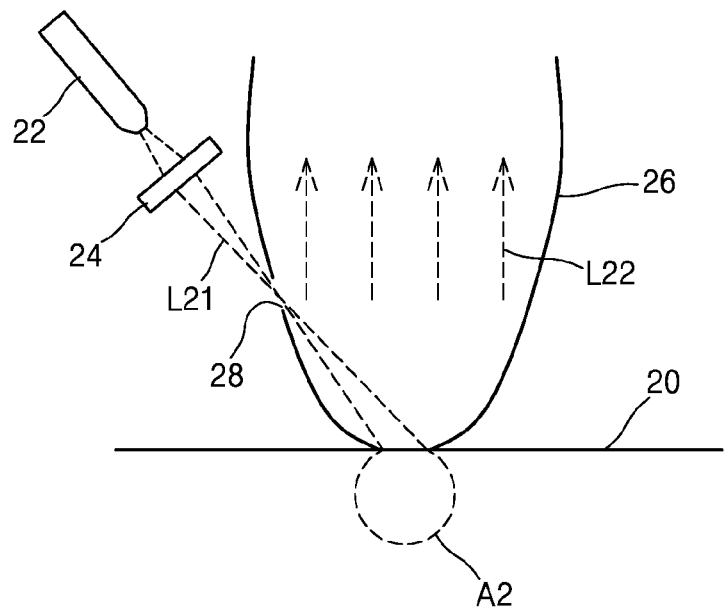
FIG. 2 is schematic view of a biometric sensor of a biometric analysis system according to an exemplary embodiment.

FIG. 2 is schematic view of the biometric sensor 11 of a biometric analysis system according to an exemplary embodiment.

Referring to FIG. 2, the biometric sensor 11 may include a light source 22 that emits light L21 onto a region A2 of interest of the object 20 under examination and a collimator 26 that causes a travel direction of diffused light L22 to be aligned in a certain direction.

The light source 22 may emit light in a near infrared region having a wavelength in a range from about 0.7 μm to about 2.5 μm, and may include an LED or a laser diode. The travel direction of the diffused light L22 may be collimated in a constant direction by the collimator 26. An opening for exposing the region A2 of interest of the object 20 may be formed on a region of the collimator 26. A focusing element 24 may be disposed on an optical path via which the light L21 emitted from the light source 22 is emitted onto the region A2 of interest of the object 20 under examination that is exposed through the region of the collimator 26. The focusing element 24 may be, for example, a focus lens. The light L21 emitted from the light source 22 may be incident onto the region A2 of interest through an appropriate focal distance control by the focusing element 24. A window (e.g., through-hole) 28 may be formed on a side of the collimator 26 on the optical path of the light L21 so that the light L21 reaches the region A2 of interest. The light L21 emitted from the light source 22 may be focused on the window 28 of the collimator 26 by the focusing element 24.

In this manner, since the focusing element 24 and the window 28 are formed on the optical path, the light L21 emitted from the light source 22 may be incident onto the entire region A2 of interest, and thus, a maximum irradiation region may be ensured. Also, an excessive exposure of the region A2 of interest to the light L21 may be prevented by adjusting the light L21 emitted to the region A2 of interest. Accordingly, an optical loss may be prevented, high efficiency spectrums may be ensured, and a signal-to-noise ratio may be improved during a biometric information analysis. The light L21 emitted onto the region A2 of interest may collide with a surface and internal molecular structure, and may be emitted as a diffused light L22, a wavelength of which is changed when the diffused light L22 is re-emitted after being absorbed in the molecular structure. The emitted diffused light L22 may be collimated in a constant direction, for example, towards the spectrometer 13 of FIG. 1 by the collimator 26.

Figure 3:
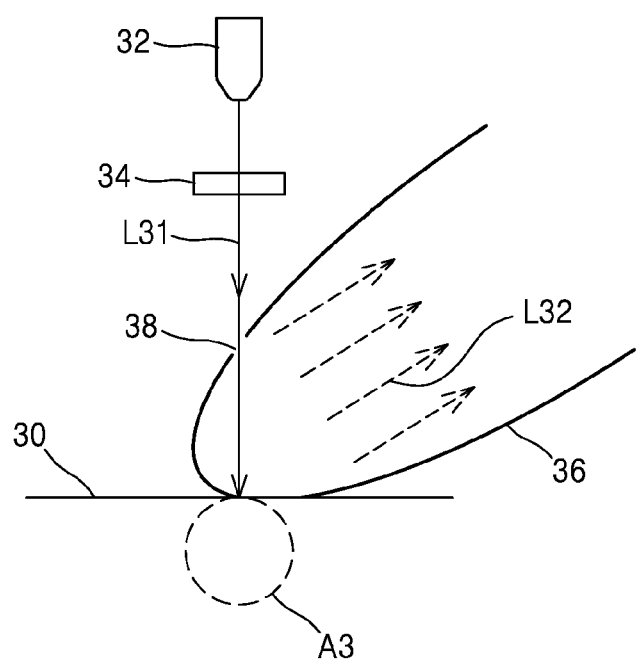
FIG. 3 is a schematic view of a biometric sensor according to another exemplary embodiment.

FIG. 3 is a schematic view of a biometric sensor according to another exemplary embodiment.

Referring to FIG. 3, a light source of the biometric sensor according to the current exemplary embodiment may include a light source 32 that emits light L31 onto a region A3 of interest of an object 30 under examination and a focusing element 34 that is formed on an optical path between the region A3 of interest and the light source 32. The biometric sensor may include a collimator 36 that adjust a travel direction of diffused light L32 reflected from the object 30 to be aligned with a spectrometer. For example, the collimator 36 may cause the travel direction of the diffused light L32 to be parallel to a lengthwise direction of the collimator 36. A region of the collimator 36 may be opened to expose the region A3 of interest to the outside. A window 38 may be formed on a side of the collimator 36 on the optical path via which the light L31 emitted from the light source 32 is incident onto the region A3 of interest.

The light L31 emitted from the light source 32 may be focused on the window 38 of the collimator 36 by the focusing element 34. The window 38 may be an opening or a through-hole placed on a side of the collimator 36, and may be a region on which the light L31 emitted from the light source 32 is focused. A width of the window 38 may be appropriately controlled and is not specifically limited. In comparison to the optical sensor of FIG. 2, in the optical sensor of FIG. 3, an incidence angle of the light L31 is almost 90° with respect to the region A3 of interest. In this manner, the optical sensor according to the current exemplary embodiment may emit the light L31 with various incidence angles to the region A3 of interest, and an optical irradiation region and optical density with respect to the object 30 may be controlled.

Figure 4:
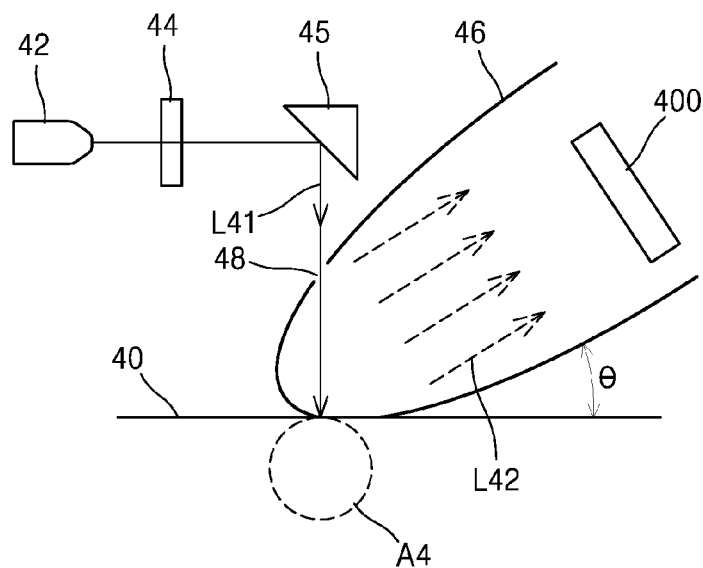
FIG. 4 is a schematic view of a biometric sensor according to another exemplary embodiment.

FIG. 4 is a schematic view of a biometric sensor according to another exemplary embodiment.

Referring to FIG. 4, a biometric sensor according to the current exemplary embodiment may include a light source unit that includes a light source 42 that emits light L41 onto an region A4 of interest of the object 40 under examination and a focusing element 44 formed on an optical path between the light source 42 and the region A4 of interest. The optical path between the light source 42 and the region A4 of interest may be variously controlled. In order to control the optical path, the biometric sensor according to the current exemplary embodiment may further include an optical path converter 45. In FIG. 4, as an example, the optical path converter 45 has a prism type. However, the optical path converter 45 may be a mirror having a flat panel type or a beam splitter.

The biometric sensor may include a collimator 46 that induces the travel direction of diffused light L42 towards a spectrometer 400. A region of the collimator 46 may be opened to expose the region A4 of interest. A window 48 may be formed on a side of the collimator 46 via which light, an optical path of which is changed by the optical path converter 45 after being emitted from the light source 42, is incident onto the region A4 of interest passing through the collimator 46. The window 48 may be a region on which the light L41 emitted from the light source 42 is focused. A width of the window 48 may be appropriately controlled, and is not specifically limited. An angle θ between the collimator 46 and a surface may be appropriately controlled to readily collimate the diffused light L42 emitted from the region A4 of interest to the spectrometer 400, and the angle θ is not specifically limited.

As described above, in the optical sensor according to the current exemplary embodiment, the optical path of the light L41 emitted from the light source 42 may be converted by the optical path converter 45 to have various optical paths. Also, the light L41 may be emitted onto the region A4 of interest with various angles, and the control of an optical irradiation region and an optical density with respect to the object 40 under examination may be possible.

Figure 5:
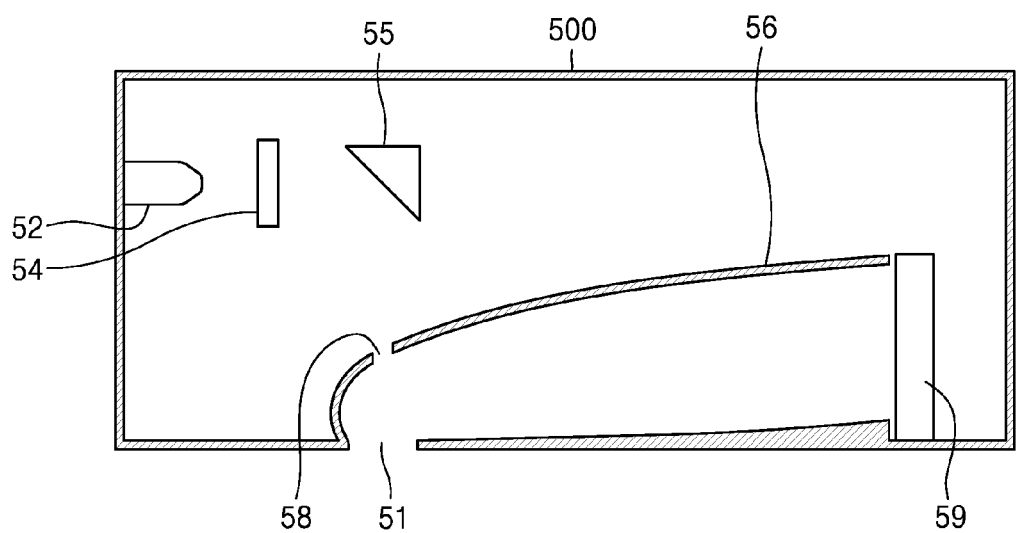
FIG. 5 is a cross-sectional view of a structure that includes an optical sensor according to an exemplary embodiment.

FIG. 5 is a cross-sectional view of a structure that includes an optical sensor according to an exemplary embodiment. The structure of FIG. 5 includes the biometric sensor of FIG. 4.

Referring to FIG. 5, the structure may include a housing 500 and a light source 52 that emits light and a focusing element 54 located on an optical path of the light emitted from the light source 52 that are located within the housing 500. The housing 500 may also include an optical path converter 55 that may change an optical path of the light emitted from the light source 52. Here, a light source unit may include the light source 52, the focusing element 54, and the optical path converter 55.

A collimator 56 may be formed on a region of the housing 500. An opening 51 may be formed on a region of the collimator 56 and the housing 500. The opening 51 may be located on a region of interest of an object under examination. A window 58 may be formed on a side of the collimator 56 via which light emitted from the light source 52 enters the opening 51. A spectrometer 59 at which diffused light emitted from the collimator 56 is collimated and focused may be formed on an edge of the collimator 56.

The housing 500 that surrounds the biometric sensor may be formed of various materials, for example, flexible materials. Also, the housing 500 may be formed of a material that blocks external light. The biometric sensor may be a wearable device to be worn on the object 10 under examination, for example, may be a bracelet type device that can be worn on a wrist. At this point, all of the constituent elements of the biometric analysis system 100 as depicted in FIG. 1 may be included in the wearable device. Also, optionally, only the structure of the light source unit 12 may be mounted in the wearable device and a signal of the diffused light L12 measured by the spectrometer 13 may be transmitted to an external device. Also, the light source unit 12 may be implemented as a wearable device and the control unit 14 may be embodied separately from the wearable device.

Figure 6:
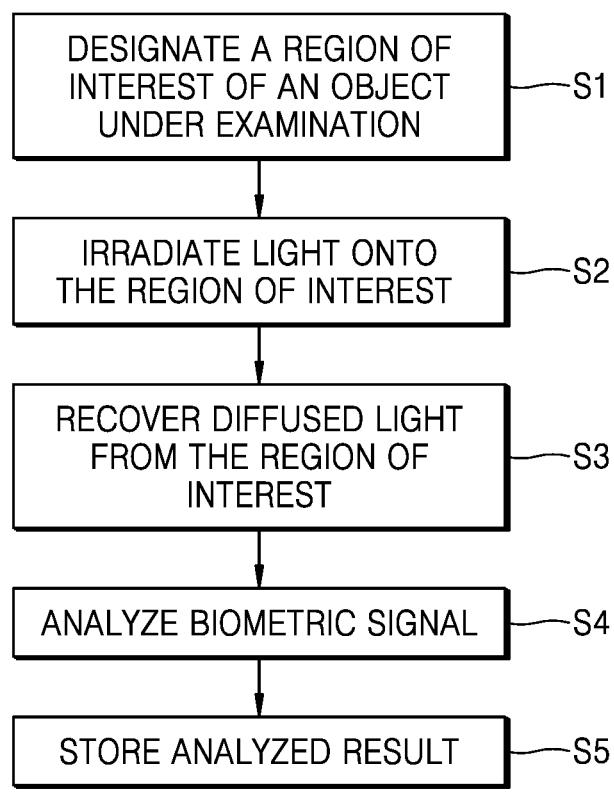
FIG. 6 is a flow chart illustrating a method of biometric analysis by using a biometric analysis system according to an exemplary embodiment.

FIG. 6 is a flow chart illustrating a method of biometric analysis by using a biometric analysis system according to an exemplary embodiment.

Referring to FIGS. 1 and 6, the region A2 of interest of the object 20 under examination may be determined to obtain biometric information from the region A2 (operation S1). For example, in order to measure a blood glucose content of a human body, a wrist portion may be designated as a region of interest. The light L21 is emitted onto the region A2 of interest from a light source of the light source unit 12 (operation S2). While the region A2 of interest is in contact with a boundary of an opening of a collimator, a laser light in a region of near infrared having a wavelength in a range from about 0.7 μm to about 2.5 μm may be emitted onto the region A2 of interest from the light source unit 12. When the light L21 is incident onto the region A2 of interest, diffused light L12 that includes biometric information of the region A2 of interest may be emitted from the region A2 of interest. The diffused light L12 is collimated by a collimator and is detected by the spectrometer 13 (operation S3).

The diffused light L12 detected by the spectrometer 13 is transmitted to the control unit 14 where biometric information or biometric signal of the region A2 of interest is analyzed (operation S4). The control unit 14 may include a signal processing unit 15 that analyzes the biometric information of the object 10 under examination from the signal that is generated from the diffused light L12 and is measured by the spectrometer 13. The signal processing unit 15 may be driven by a microprocessor. The signal processing unit 15 may analyze properties of the object 10 under examination by using the Raman Spectroscopy or a method of analyzing a near infrared ray absorption spectrum. When the light L21 is emitted into the object 10 under examination, the light L21 is diffused in various directions after colliding with atoms or molecules in the object 10 under examination. The Raman Spectroscopy uses the diffusion, in particular, inelastic scattering of the light L21 in various directions. Here, inelastic scattering denotes the emission of light after being absorbed by the atoms or molecules as opposed to merely a simple reflection at surfaces of atoms or molecules. The diffused light L12 emitted from the object 10 under examination may have a relatively longer wavelength than that of the incident light L21, and a wavelength difference between the light L21 and the diffused light L12 may be approximately below 200 nm. Various properties, such as vibration of molecules and a structure of molecules in the object 10 under examination may be detected by analyzing a spectrum of the diffused light L12. The control unit 14 may further include the user interface 16, and the user interface 16 may further include an input unit through which various commands are inputted in a process of analyzing biometric information and a display unit on which a biometric analyzing process and the result are visually displayed.

Next, the analysis result of the biometric information of the object 10 under examination may be stored in the storage unit 18 by the control unit 14. Optionally, after analyzing the biometric information of the object 10 under examination by the control unit 14, a process for comparing the measured biometric information with biometric information of the object 10 under examination stored in advance may be performed. The results of the comparison and evaluation may be restored in the storage unit 18.

The biometric sensor according to an exemplary embodiment may prevent an optical loss of diffused light that is emitted from an object under examination after emitting the light from a light source onto a region of interest of the object under examination.

Since a focusing element and a window are formed on an optical path of light that is emitted from a light source onto an object under examination, a required irradiation region may be ensured and an excessive exposure to light may be prevented.

Also, a high efficiency spectrum may be ensured and a signal-to-noise ratio may be improved.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A biometric sensor comprising:
    a light source configured to emit light toward a region of interest of an object under examination, the light being diffused at the region of interest;
    a collimator comprises a through-hole, the collimator being configured to collimate the diffused light received from the region of interest;
    a focus lens that is disposed on an optical path of the light between the light source and the through-hole of the collimator and is configured to control a focal distance of the light to focus the light emitted from the light source onto the through-hole of the collimator, the light entering through the through-hole traveling to the region of interest of the object; and
    a spectrometer configured to analyze the diffused light transmitted by the collimator.

2. The biometric sensor of claim 1, wherein the light emitted by the light source has a wavelength in a range from about 0.7 µm to about 2.5 µm.

3. The biometric sensor of claim 1, further comprising an optical path converter configured to control the optical path of the light emitted by the light source.

4. The biometric sensor of claim 1, wherein the collimator further comprises an opening via which the light emitted by the light source is incident on the region of interest and the light diffused from the region of interest of the object is collected.

5. The biometric sensor of claim 4, wherein the collimator is a compound parabolic concentrator type collimator.

* * * * *